(12) United States Patent
Sun et al.

(10) Patent No.: US 10,023,577 B2
(45) Date of Patent: Jul. 17, 2018

(54) CRYSTALLINE FORM OF JAK KINASE INHIBITOR BISULFATE AND A PREPARATION METHOD THEREOF

(71) Applicant: Jiangsu Hengrui Medicine Co., Ltd., Lianyungang, Jiangsu (CN)

(72) Inventors: Piaoyang Sun, Jiangsu (CN); Guaili Wu, Jiangsu (CN); Quanliang Zhang, Jiangsu (CN); Yongjiang Chen, Jiangsu (CN); Lingjia Shen, Jiangsu (CN)

(73) Assignee: JIANGSU HENGRUI CO., LTD., Lianyungang, Jiangsu (CN)

( * ) Notice: Subject to any disclaimer, the term of this patent is extended or adjusted under 35 U.S.C. 154(b) by 0 days.

(21) Appl. No.: 15/522,991

(22) PCT Filed: Oct. 9, 2015

(86) PCT No.: PCT/CN2015/091527
§ 371 (c)(1),
(2) Date: Apr. 28, 2017

(87) PCT Pub. No.: WO2016/070697
PCT Pub. Date: May 12, 2016

(65) Prior Publication Data
US 2017/0313709 A1    Nov. 2, 2017

(30) Foreign Application Priority Data

Nov. 5, 2014  (CN) .......................... 2014 1 0617808

(51) Int. Cl.
*A01N 43/90* (2006.01)
*A61K 31/519* (2006.01)
*C07D 487/04* (2006.01)

(52) U.S. Cl.
CPC ........ *C07D 487/04* (2013.01); *C07B 2200/13* (2013.01)

(58) Field of Classification Search
CPC .................................................. A61K 31/519
USPC ..................................................... 514/265.1
See application file for complete search history.

(56) References Cited

U.S. PATENT DOCUMENTS 9,527,851 B2 * 12/2016 Zhang .................... A61K 45/06

FOREIGN PATENT DOCUMENTS

| CN | 105566327 A | 5/2016 | |
| WO | 2012171863 A1 | 12/2012 | |
| WO | 2013091539 A1 | 6/2013 | |
| WO | WO2013091539 * | 6/2013 | ........... C07D 487/04 |
| WO | 2014194741 A1 | 12/2014 | |

* cited by examiner

Primary Examiner — Jeffrey H Murray
(74) Attorney, Agent, or Firm — Panitch Schwarze Belisario & Nadel LLP (57) ABSTRACT

A crystal form of JAK kinase inhibitor bisulfate and a preparation method thereof are provided. In particular, a type II crystal of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate and a preparation method thereof are described. The preparation method includes steps of crystallizing any solid crystal form or amorphous compound of formula (I) in a single organic solvent or a mixed organic solvent to obtain a type II crystal form of the compound of formula (I). The type II crystal form of the compound of formula (I) obtained by the described methods has good crystal stability and chemical stability. In addition, the solvent used for crystallization has low toxicity and residue, which is better suited for use in clinical treatment.

Formula (I)

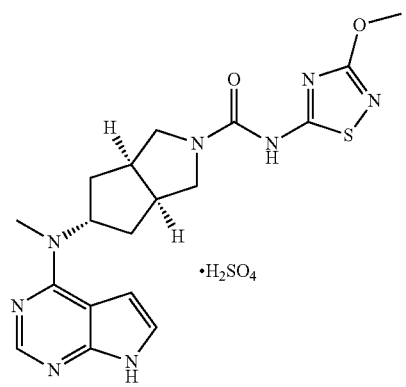

19 Claims, 4 Drawing Sheets

CRYSTALLINE FORM OF JAK KINASE INHIBITOR BISULFATE AND A PREPARATION METHOD THEREOF

CROSS-REFERENCE TO RELATED APPLICATION

This application is a Section 371 of International Application No. PCT/CN2015/091527, filed Oct. 9, 2015, which was published in the Chinese language on May 12, 2016 under International Publication No. WO 2016/070697 A1, and the disclosure of which is incorporated herein by reference.

FIELD OF THE INVENTION

The present invention relates to crystal form II of (3aR, 5s,6aS)—N-(3-methoxyl-1,2,4-thiadiazole-5-yl)-5-(methyl (7H-pyrrolo[2,3-d]pyrimidine-4-yl)amino)hexahydrocyclopenta[c]pyrrole-2(1H)-formamide bisulfate, a preparation thereof, and use thereof. The compound of formula (I) prepared according to the method of the present invention can be used for the treatment of arthritis.

BACKGROUND OF THE INVENTION

Arthritis is the most common chronic disease in the world There are many causes of arthritis, and the causes of joint damage are also different. Currently, Tofacitinib (CP-690550) is a novel oral JAK (Janus Kinase) pathway inhibitor developed by Pfizer Inc. Tofacitinib is a first-in-class drug developed for rheumatoid arthritis treatment. Based on the structure of tofacitinib, a series of JAK inhibitor compounds, which are active in vitro and in vivo and highly absorbable, have been developed. See WO2013091539. The compounds disclosed in WO2013091539 were screened and prepared as salts in which (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate of formula (I) was obtained, and its preparation method was disclosed in PCT Patent Application No. PCT/CN2014/076794 (an application previously filed by the applicant).

Formula (I)

SHR0302 tofacitinib

It is well known that the crystal structure of a pharmaceutically active ingredient often affects the chemical stability of the drug. Different crystallization conditions and storage conditions can lead to changes in the crystal structure of the compound, and sometimes the accompanying production of other crystal forms. The compound of formula (I) was dissolved in methanol, and then part of the solvent was evaporated to precipitate a crystal, which was named crystal form I. See Chinese Patent Application No. 201410529863.8. In the subsequent study, we surprisingly found that the compound also has another crystal form. When the salt is refluxed in a multisolvent system to produce a crystal transformation, or crystallized in a variety of solvents, another crystal is obtained, which is defined as crystal form II herein. Studies on the factors that influence crystal forms and the specific stability tests showed that the crystal stability of crystal form II is good, and this crystal form is the most easily obtained stable crystal form of the compound. Its preparation process is controllable and repeatable, thus it is more suitable for industrial production.

SUMMARY OF THE INVENTION

The purpose of the present invention is to provide a stable crystal form of a bisulfate of the compound of formula (I) as a JAK inhibitor and the preparation method thereof.

Figure 1:
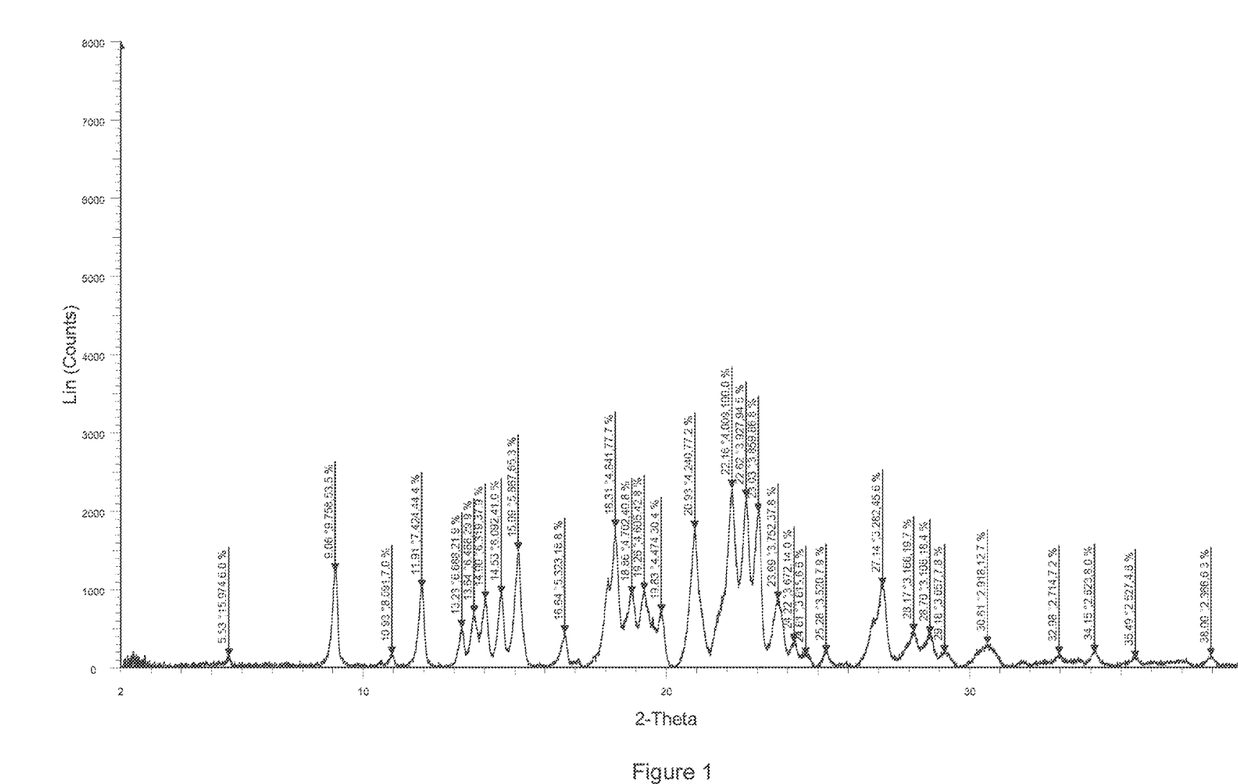
FIG. 1 shows the X-ray powder diffraction spectrum of crystal form II of the compound of formula (I) (represented by the symbol SHR0302 in the figure)

The inventor has tested a series of crystal products of the compound of formula (I) obtained under various conditions by X-ray diffraction and differential scanning calorimetry (DSC) test. It was found that a stable crystal form of the compound of formula (I), which is called as crystal form II, can be obtained under the crystallization condition according to the present invention. The DSC spectrum of crystal form II of the compound of formula (I) according to the present application shows a melting endothermic peak at about 218° C. The X-ray powder diffraction spectrum, which was obtained by using Cu—Ka radiation and represented by 2θ angle and interplanar distance (d value), is shown in FIG. 1 in which there are characteristic peaks at 8.96 (9.87), 11.80 (7.50), 13.12 (6.74), 13.53 (6.54), 13.89 (6.37), 14.42 (6.14), 14.98 (5.91), 16.52 (5.36), 18.20 (4.87), 18.75 (4.73), 19.15 (4.63), 19.72 (4.50), 20.82 (4.26), 22.05 (4.03), 22.52 (3.95), 22.92 (3.88), 23.58 (3.77) and 27.04 (3.30).

In the preparation method of crystal form II of the present invention, the existing forms of the compound of formula (I) that can be used as a starting material is not particularly limited, and any crystal form or amorphous solid can be used. The preparation method of crystal form II of the compound of formula (I) of the present invention comprises:

using one or more lower organic solvents, preferably polar organic solvents with fewer carbon atoms and higher volatility, which can be used as crystallization solvents, such as alcohols, ketones, esters, halogenated hydrocarbons or a mixture thereof; more preferably, methanol, ethanol, isopropanol, ethyl acetate, acetone, dichloromethane or a mixture thereof as the crystallization solvents. The crystallization solvent can be a single solvent or a mixed solvent comprising the solvents mentioned above.

Specifically, the present invention provides the preparation method of crystal form II of the compound of formula (I) comprising the following steps of:

(1) dissolving (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide into an organic solvent, then adding concentrated sulfuric acid dropwise, filtering the solution and precipitating a crystal; or dissolving a solid of the compound of formula (I) into an appropriate amount of organic solvent under heating, then cooling the solution to precipitate a crystal; and (2) filtering the crystal, then washing and drying it.

In a preferred embodiment of the present invention, the organic solvent in step (I) is selected from any one of alcohols, ketones, esters having 3 or less carbon atoms, or a mixed solvent of one or more solvents mentioned above and a halogenated hydrocarbon having 3 or less carbon atoms. More preferably, the organic solvent is selected from methanol, ethanol, isopropanol, acetone, ethyl acetate, or a mixed solvent system such as dichloromethane/methanol, dichloromethane/methanol/ethanol, dichloromethane/methanol/isopropanol, dichloromethane/methanol/ethyl acetate, or dichloromethane/methanol/acetone.

Most preferably, the single solvent is methanol.

In another preferred embodiment of the present invention, the mixed solvent is dichloromethane/methanol/ethanol, and the ratio of the three is not particularly limited. In a preferred embodiment of the present invention, the ratio of the three is 12:3:10.

The recrystallization method is not particularly limited and can be carried out by a conventional recrystallization process. For example, any form of the compound of formula (I) can be dissolved in an organic solvent under heating, and then the solution is cooled slowly and stirred to precipitate a crystal. After the completion of crystallization, the resulting product is filtered and dried to obtain the desired crystal. The crystal obtained by filtration is usually dried in a vacuum under reduced pressure at a heating temperature of about 30 to 100° C., preferably 40 to 60° C., to remove the recrystallization solvent.

The resulting crystal form of the compound of formula (I) is determined by DSC and X-ray diffraction spectrum. Meanwhile, the residual solvent of the obtained crystal is also determined.

Crystal form II of the compound of formula (I) prepared according to the present method does not contain or contains only a relatively low content of residual solvent, which meets the requirement of the National Pharmacopoeia concerning the limitation of residual solvent in drug products. Thus, the crystal of the present invention is suitable for use as a pharmaceutical active ingredient.

The research results show that the stability of the crystal form II of the compound of formula (I) prepared by the present invention is significantly better than that of the amorphous sample under the conditions of high temperature and high humidity. Moreover, crystal form II has good stability under the conditions of grinding, pressure and heating which meets the production, transportation and storage requirements of drug products. The preparation process of crystal form II is stable, repeatable and controllable, and is suitable for industrial production.

The present invention also provides a pharmaceutical composition comprising crystal form II of the compound of formula (I) and at least one pharmaceutically acceptable carrier. The pharmaceutically acceptable carrier is selected from at least one of lactose, mannitol, microcrystalline cellulose, croscarmellose sodium, sodium carboxymethyl starch, hydroxypropyl methyl cellulose, povidone, and magnesium stearate. The content of crystal form II in the pharmaceutical composition of the present invention is 0.5 mg to 200 mg.

The present invention further relates to use of crystal form II of the compound of formula (I) or the pharmaceutical composition of the present invention in the preparation of a medicament for the treatment of JAK-related disease, preferably rheumatic and rheumatoid arthritis.

DETAILED DESCRIPTION OF THE INVENTION

The present invention is illustrated by the following examples in detail, but the examples of the invention are only intended to describe the technical solution of the invention, and should not be considered as limiting the scope of the present invention.

Test instruments used in the experiments

1. DSC spectrum

Instrument type: Mettler Toledo DSC 1 Stare$^e$ System
Purging gas: Nitrogen
Heating rate: 10.0° C./min
Temperature range: 40-300° C.

2. X-ray diffraction spectrum

Instrument type: D/Max-RA Japan Rigaku X-ray powder diffractometer
Rays: monochromatic Cu-Kα rays (λ=1.5418 Å)
Scanning mode: θ/2θ, Angular range: 2-40°
Voltage: 40 KV Electric Current: 40 mA Example 1

1.0 g (2.4 mmol) of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide was added to a 50 ml erlenmeyer flask, followed by addition of 12 ml of dichloromethane and 3 ml of anhydrous methanol. The reaction mixture was stirred at room temperature, then 0.25 g (2.5 mmol) of concentrated sulfuric acid was added dropwise. After the suspension became clear, the insolubles were removed by filtration. No solid was precipitated after the filtrate was stirred for 6 hours. 10 ml of isopropanol were added, then a large amount of white solid was precipitated. The reaction mixture was stirred for another 18 hours, filtered and dried to obtain 1.138 g of a white solid in 92.1% yield. The X-ray diffraction spectrum of this crystal sample is shown in FIG. 1 in which there are characteristic peaks at 8.96 (9.87), 11.80 (7.50), 13.12

Figure 2:
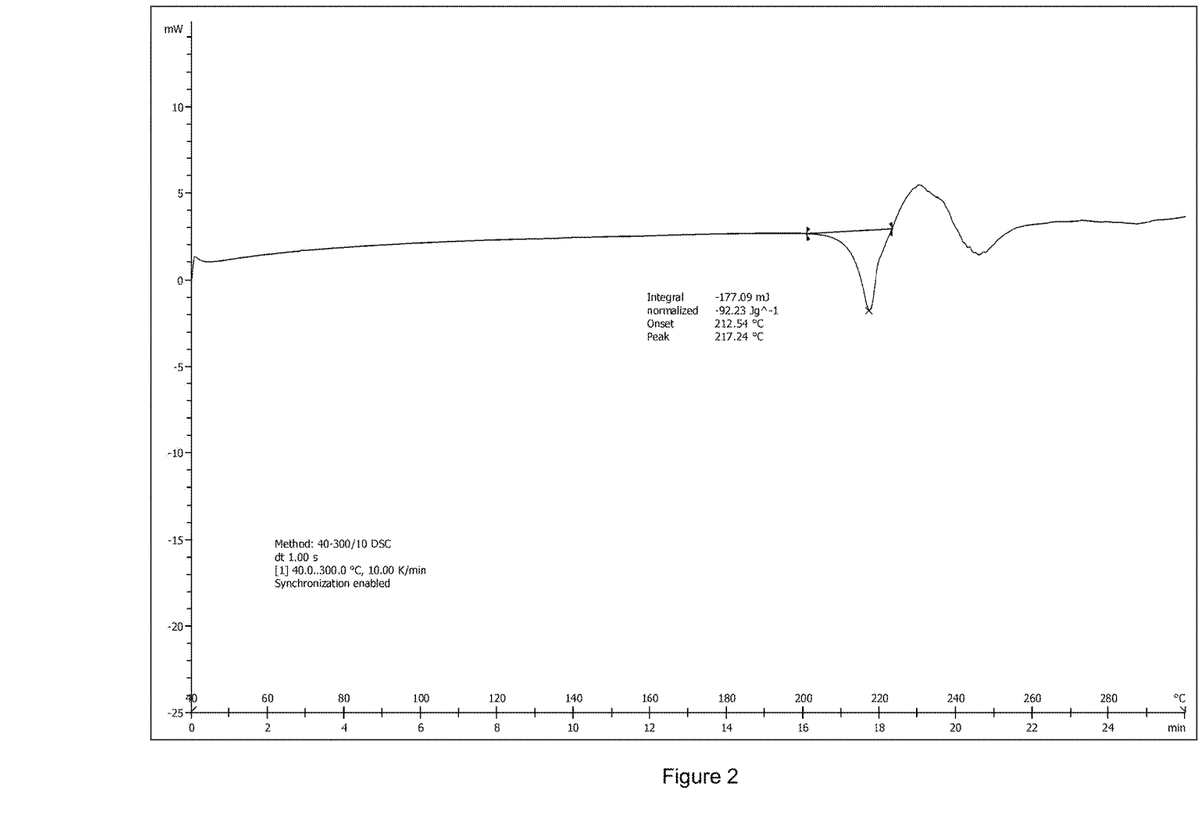
FIG. 2 shows the DSC spectrum of crystal form II of the compound of formula (I)

(6.74), 13.53 (6.54), 13.89 (6.37), 14.42 (6.14), 14.98 (5.91), 16.52 (5.36), 18.20 (4.87), 18.75 (4.73), 19.15 (4.63), 19.72 (4.50), 20.82 (4.26), 22.05 (4.03), 22.52 (3.95). 22.92 (3.88), 23.58 (3.77) and 27.04 (3.30). The DSC spectrum is shown in FIG. 2, having a melting endothermic peak at 217.24° C. The crystal form was defined as crystal form II.

Example 2

Figure 3:
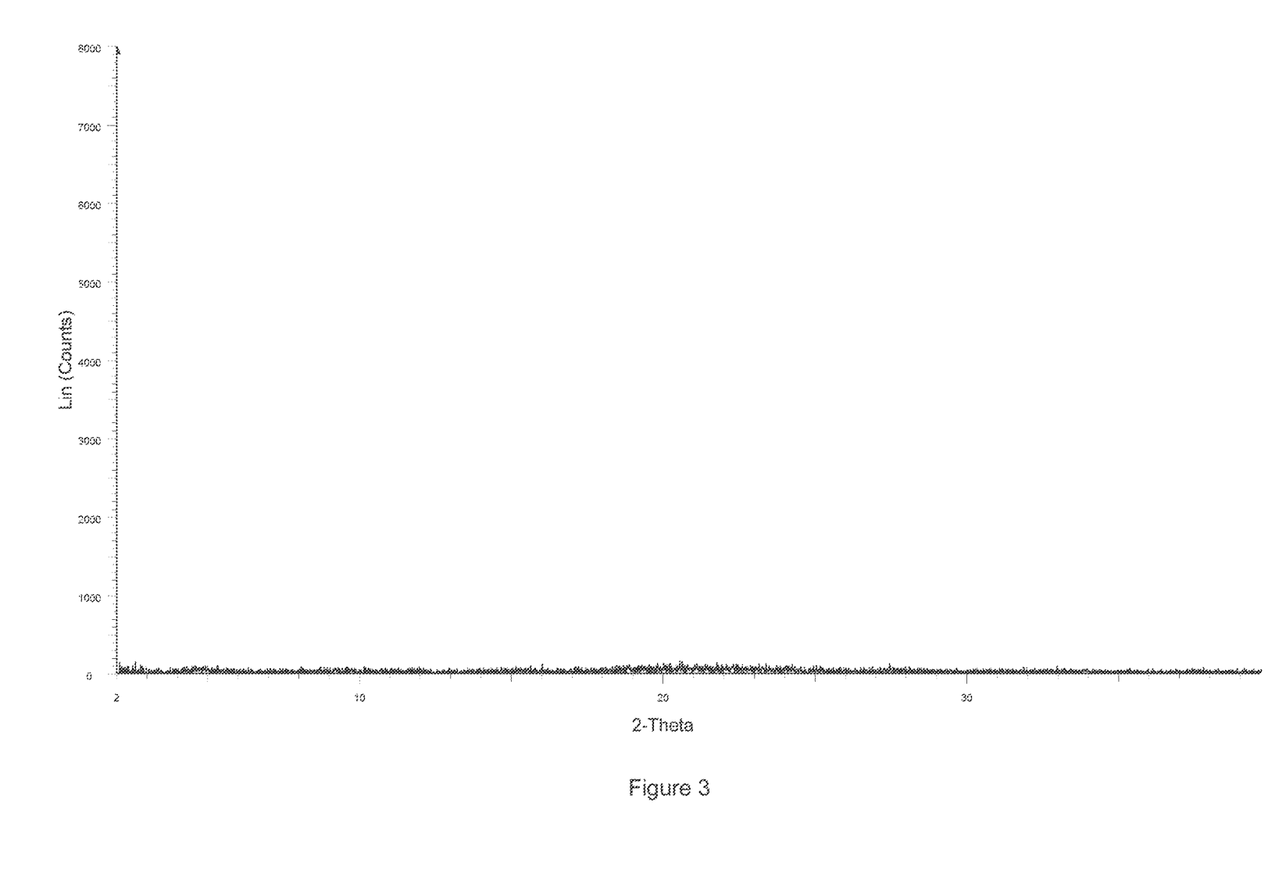
FIG. 3 shows the X-ray powder diffraction spectrum of the amorphous solid of the compound of formula (I)
Figure 4:
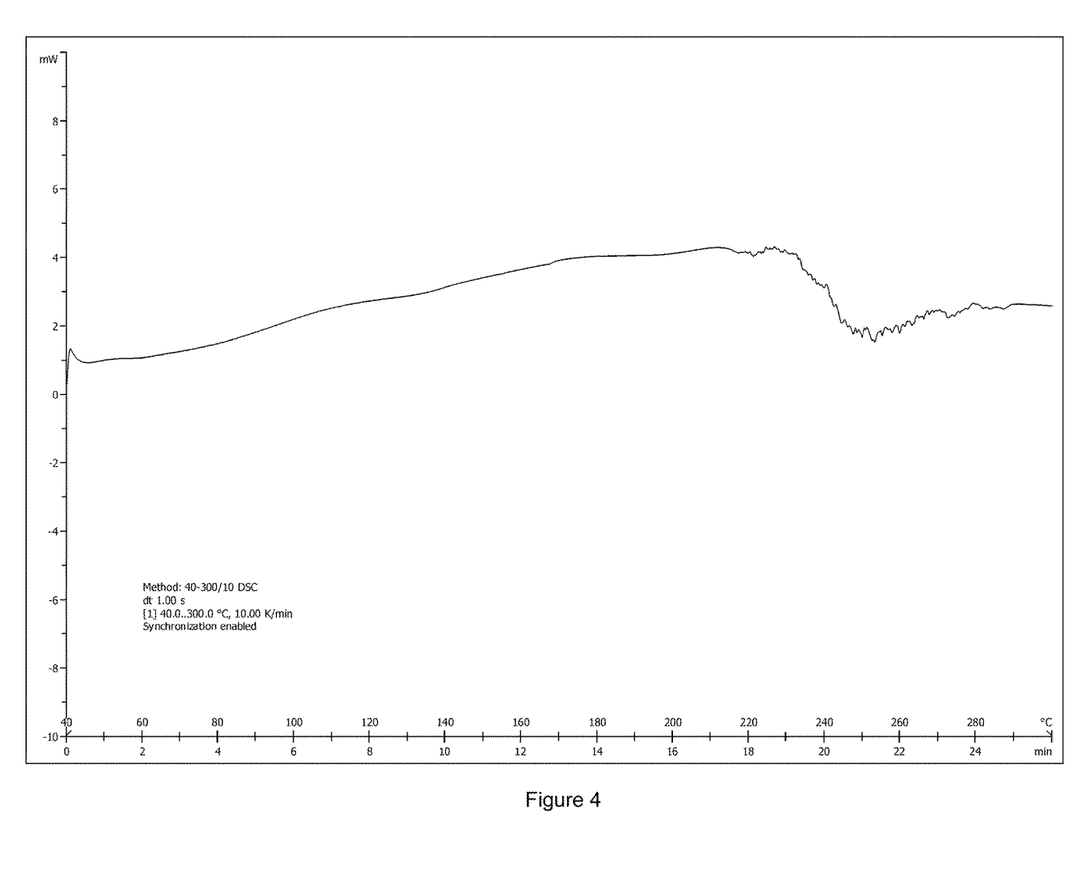
FIG. 4 shows the DSC spectrum of the amorphous solid of the compound of formula (I).

1.0 g (2.4 mmol) of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide was added to a 50 ml erlenmeyer flask, followed by addition of 12 ml of dichloromethane and 3 ml of anhydrous methanol. The reaction mixture was stirred at room temperature, then 0.25 g (2.5 mmol) of concentrated sulfuric acid was added dropwise. After the suspension became clear, the insolubles were removed by filtration, and the filtrate was concentrated to dryness to obtain the compound of formula (I) in an amorphous form. The X-ray diffraction spectrum of the solid sample is shown in FIG. 3 in which there are no characteristic absorption peaks of a crystal. The DSC spectrum of the solid sample is shown in FIG. 4.

Example 3

1.0 g (2.4 mmol) of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide was added to a 50 ml erlenmeyer flask, followed by addition of 12 ml of dichloromethane and 3 ml of anhydrous methanol. The reaction mixture was stirred at room temperature, then 0.25 g (2.5 mmol) of concentrated sulfuric acid was added dropwise. After the suspension became clear, the insolubles were removed by filtration, and the filtrate was stirred for 24 hours to precipitate a crystal, filtered and dried to obtain 1.15 g of a white solid in 93.2% yield. The product was identified as crystal form II after studying and comparing the X-ray diffraction and DSC spectra.

Example 4

1.0 g (2.4 mmol) of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide was added to a 50 ml erlenmeyer flask, followed by addition of 12 ml of dichloromethane and 3 ml of anhydrous methanol. The reaction mixture was stirred at room temperature, then 0.25 g (2.5 mmol) of concentrated sulfuric acid was added dropwise. After the suspension became clear, the insolubles were removed by filtration. No solid was precipitated after the filtrate was stirred for 6 hours. 10 ml of ethanol were added, then a large amount of white solid was precipitated. The reaction mixture was stirred for another 18 hours, filtered and dried to obtain 1.17 g of a white solid in 94.9% yield. The product was identified as crystal form II after studying and comparing the X-ray diffraction and DSC spectra.

Example 5

1.0 g (2.4 mmol) of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide was added to a 50 ml erlenmeyer flask, followed by addition of 12 ml of dichloromethane and 3 ml of anhydrous methanol. The reaction mixture was stirred at room temperature, then 0.25 g (2.5 mmol) of concentrated sulfuric acid was added dropwise. After the suspension became clear, the insolubles were removed by filtration. No solid was precipitated after the filtrate was stirred for 6 hours. 5 ml of ethyl acetate were added, then a large amount of white solid was precipitated. The reaction mixture was stirred for another 18 hours, filtered and dried to obtain 1.16 g of a white solid in 94.2% yield. The product was identified as crystal form II after studying and comparing the X-ray diffraction and DSC spectra.

Example 6

1.0 g (2.4 mmol) of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide was added to a 50 ml erlenmeyer flask, followed by addition of 12 ml of dichloromethane and 3 ml of anhydrous methanol. The reaction mixture was stirred at room temperature, then 0.25 g (2.5 mmol) of concentrated sulfuric acid were added dropwise. After the suspension became clear, the insolubles were removed by filtration. No solid was precipitated after the filtrate was stirred for 6 hours. 5 ml of acetone were added, then a large amount of white solid was precipitated. The reaction mixture was stirred for another 18 hours, filtered and dried to obtain 1.14 g of a white solid in 92.3% yield. The product was identified as crystal form II after studying and comparing the X-ray diffraction and DSC spectra.

Example 7

1.0 g (2.4 mmol) of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide was added to a 50 ml erlenmeyer flask, followed by addition of 12 ml of dichloromethane and 3 ml of anhydrous methanol. The reaction mixture was stirred at room temperature, then 0.25 g (2.5 mmol) of concentrated sulfuric acid were added dropwise. After the suspension became clear, the insolubles were removed by filtration, and the filtrate was concentrated to dryness to obtain the compound of formula (I) in an amorphous form. The resulting sample was added to 5 ml of methanol, then the mixture was heated to reflux for 20 minutes, cooled, stirred for 2 hours to produce a crystal transformation, filtered and dried to obtain 942 mg of a white solid in 76.2% yield. The product was identified as crystal form II after studying and comparing the X-ray diffraction and DSC spectra.

Example 8

The compound of formula (I) in an amorphous form was prepared from 1.0 g (2.4 mmol) of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide according to the experimental method of Example 2. The resulting sample was added to 5 ml of ethanol, then the mixture was heated to reflux until the solution was clear. The solution was refluxed for another 20 minutes, cooled, stirred for 2 hours to produce a crystal transformation, filtered and dried to obtain 1.08 g of a white solid in 82.3% yield. The product was identified as crystal form II after studying and comparing the X-ray diffraction and DSC spectra.

Example 9

The compound of formula (I) in an amorphous form was prepared from 1.0 g (2.4 mmol) of (3aR,5s,6aS)—N-(3- methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide according to the experimental method of Example 2. The resulting sample was added to 5 ml of isopropanol, then the mixture was heated to reflux until the solution was clear. The solution was refluxed for another 20 minutes, cooled, stirred for 2 hours to produce a crystal transformation, filtered and dried to obtain 1.05 g of a white solid in 85.0% yield. The product was identified as crystal form II after studying and comparing the X-ray diffraction and DSC spectra.

Example 10

The compound of formula (I) in an amorphous form was prepared from 1.0 g (2.4 mmol) of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide according to the experimental method of Example 2. The resulting sample was added to 5 ml of ethyl acetate, then the mixture was heated to reflux until the solution was clear. The solution was refluxed for another 20 minutes, cooled, stirred for 2 hours to produce a crystal transformation, filtered and dried to obtain 1.11 g of a white solid in 90.1% yield. The product was identified as crystal form II after studying and comparing the X-ray diffraction and DSC spectra.

Example 11

The compound of formula (I) in an amorphous form was prepared from 1.0 g (2.4 mmol) of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide according to the experimental method of Example 2. The resulting sample was added to 5 ml of acetone, then the mixture was heated to reflux until the solution was clear. The solution was refluxed for another 20 minutes, cooled, stirred for 2 hours to produce a crystal transformation, filtered and dried to obtain 1.13 g of a white solid in 91.5% yield. The product was identified as crystal form II after studying and comparing the X-ray diffraction and DSC spectra.

Example 12

1.0 g (2.4 mmol) of the compound of formula (I) (crystal form II), which was prepared according to the method of Chinese Patent Application No. 201410529863.8, and 100 ml of methanol were added to a 250 ml one-necked flask, and heated to reflux until the solution was clear. Then, the solution was refluxed for another 10 minutes, and cooled. About 90 ml of methanol were removed by evaporation under reduced pressure, then the mixture was stirred at room temperature for 4 hours, filtered and dried to obtain 842 mg of a white solid in 84.2% yield. The product was identified as crystal form II after studying and comparing the X-ray diffraction and DSC spectra.

Example 13

Crystal form II prepared in Example 1 and the amorphous sample prepared in Example 2 were spread flat in the air to test their stability in conditions of lighting (4500 Lux), heating (40° C., 60'C.), and high humidity (RH 75%, RH 90%). Sampling times of 5 days and 10 days were studied, and the purity as detected by HPLC is shown in Table 1.

TABLE 1

Comparing the stability of crystal form II and an amorphous sample of the compound of formula (I)

| Bach number | Time (Day) | Lighting | 40° C. | 60° C. | RH 75% | RH 90% |
|---|---|---|---|---|---|---|
| Crystal | 0 | 99.30% | 99.30% | 99.30% | 99.30% | 99.30% |
| form II | 5 | 99.29% | 99.30% | 99.20% | 99.31% | 99.31% |
| 20130107 | 10 | 99.30% | 99.28% | 99.15% | 99.28% | 99.31% |
| Amorphous | 0 | 98.33% | 98.33% | 98.33% | 98.33% | 98.33% |
| Form | 5 | 98.04% | 97.65% | 94.53% | 98.32% | 99.14% |
| 20120918 | 10 | 97.51% | 96.61% | 92.12% | 98.16% | 99.12% |

After crystal form II and the amorphous sample of the compound of formula (I) were spread flat in the air to test their stability under the conditions of lighting, high temperature, and high humidity, the results of the stability study showed that high humidity does not have much effect on the two examples, but under the conditions of lighting and high temperature, the stability of crystal form II is significantly better than that of the amorphous sample.

Example 14

Crystal form II of the compound of formula (I) prepared according to the method of Example 1 was ground, heated and pressed. The results showed that the crystal form is stable. The detailed experimental data are shown in Table 2 below.

TABLE 2

Special stability study of crystal form II of the compound of formula (I)

| Batch number | Treatment Process | Experimental procedure | Crystal form | DSC peak |
|---|---|---|---|---|
| Experiment 14.1 S011113120822G | Grinding Treatment for 10 minutes | 1 g of crystal form II of the compound of formula (I) was grinded for 10 minutes in a mortar under nitrogen atmosphere. | Crystal form II | DSC peak 217.98° C. |
| Experiment 14.2 S011113120822H | Heating treatment at 80° C. for 3 hours | 1 g of crystal form II of the compound of formula (I) was spread flat and heated at 80° C. for 3 hours. | Crystal form II | DSC peak 218.45° C. |

TABLE 2-continued

Special stability study of crystal form II of the compound of formula (I)

| Batch number | Treatment Process | Experimental procedure | Crystal form | DSC peak |
|---|---|---|---|---|
| Experiment 14.3 S011113120822P | Pressing treatment | Crystal form II of the compound of formula (I) was pressed to a slice. | Crystal form II | DSC peak 217.85° C. |

What is claimed is:

1. A crystal form of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate, wherein the crystal has a characteristic X-ray powder diffraction (XRPD) spectrum comprising diffraction peaks at angles (2θ±0.2°) of 9.06, 11.91, 15.09, 18.31, 20.93, 22.16, 22.62, 23.03, and 27.14.

2. The crystal form of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate according to claim 1, wherein the crystal has a differential scanning calorimetry (DSC) spectrum comprising an endothermic melting peak at about 217.24° C.

3. A pharmaceutical composition comprising the crystal form of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate according to claim 1 and at least one pharmaceutically acceptable carrier.

4. The pharmaceutical composition according to claim 3, having an amount of the crystal form of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate of 0.5 mg to 200 mg.

5. The pharmaceutical composition according to claim 3, wherein the pharmaceutically acceptable carrier is selected from at least one of lactose, mannitol, microcrystalline cellulose, croscarmellose sodium, sodium carboxymethyl starch, hydroxypropyl methyl cellulose, povidone, and magnesium stearate.

6. A preparation method of the crystal form of (3aR,5s,6aS)—N-(3-methoxyl-1,2,4-thiadiazole-5-yl)-5-(methyl (7H-pyrrolo[2,3-d]pyrimidine-4-yl)amino)hexahydrocyclopenta[c]pyrrole-2(1H)-formamide bisulfate according to claim 1, comprising the following steps of:
(a) dissolving any crystal form or amorphous form of (3aR,5s,6aS)—N-(3-methoxyl-1,2,4-thiadiazole-5-yl)-5-(methyl(7H-pyrrolo[2,3-d]pyrimidine-4-yl)amino) hexahydrocyclopenta[c]pyrrole-2(1H)-formamide in an organic solvent to obtain a mixture, then adding concentrated sulfuric acid dropwise to the mixture to precipitate the crystal form, or adding an anti-solvent to the mixture to precipitate the crystal form;
or dissolving a solid of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate in any crystal form or amorphous form in an organic solvent under heating, then cooling the solution to precipitate the crystal form, wherein the organic solvent is selected from the group consisting of alcohols, ketones, esters having 3 or less carbon atoms, or a mixed solvent thereof, and a halogenated hydrocarbon having 3 or less carbon atoms; and
(b) filtering the crystal form, then washing and drying it.

7. The preparation method according to claim 6, wherein the organic solvent in step (a) is methanol, ethanol, isopropanol, acetone, ethyl acetate, a mixture of dichloromethane and methanol, a mixture of dichloromethane, methanol and ethanol, a mixture of dichloromethane, methanol and isopropanol, a mixture of dichloromethane, methanol and ethyl acetate, or a mixture of dichloromethane, methanol and acetone.

8. The preparation method according to claim 7, wherein the organic solvent is methanol or a mixture of dichloromethane, methanol and ethanol.

9. The preparation method according to claim 8, wherein the organic solvent has a ratio of dichloromethane:methanol:ethanol of about 12:3:10.

10. An isolated crystal form of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate, wherein the crystal has a characteristic X-ray powder diffraction (XRPD) spectrum comprising diffraction peaks at angles (2θ±0.2°) of 9.06, 11.91, 13.23, 13.64, 14.00, 14.53, 15.09, 16.64, 18.31, 18.86, 19.26, 19.83, 20.93, 22.16, 22.62, 23.03, 23.69, and 27.14.

11. An isolated crystal form of (3aR,5s,6aS)—N-(3-methoxyl-1,2,4-thiadiazole-5-yl)-5-(methyl(7H-pyrrolo[2,3-d]pyrimidine-4-yl)amino)hexahydrocyclopenta[c]pyrrole-2(1H)-formamide bisulfate, wherein the crystal has an X-ray powder diffraction (XRPD) spectrum as shown in FIG. 1.

12. A pharmaceutical composition comprising the isolated crystal form of (3aR,5s,6aS)—N-(3-methoxyl-1,2,4-thiadiazole-5-yl)-5-(methyl(7H-pyrrolo[2,3-d]pyrimidine-4-yl) amino)hexahydrocyclopenta[c]pyrrole-2(1H)-formamide bisulfate according to claim 10 and at least one pharmaceutically acceptable carrier.

13. A pharmaceutical composition comprising the isolated crystal form of (3aR,5s,6aS)—N-(3-methoxyl-1,2,4-thiadiazole-5-yl)-5-(methyl(7H-pyrrolo[2,3-d]pyrimidine-4-yl) amino)hexahydrocyclopenta[c]pyrrole-2(1H)-formamide bisulfate according to claim 11 and at least one pharmaceutically acceptable carrier.

14. A method of inhibiting a Janus kinase (JAK) in a subject in need thereof, the method comprising administering to the subject the pharmaceutical composition of claim 3.

15. The method according to claim 14, wherein the subject is in need of treatment of rheumatic arthritis or rheumatoid arthritis.

16. A method of inhibiting a Janus kinase (JAK) in a subject in need thereof, the method comprising administering to the subject the pharmaceutical composition of claim 12.

17. The method according to claim 16, wherein the subject is in need of treatment of rheumatic arthritis or rheumatoid arthritis.

18. A method of inhibiting a Janus kinase (JAK) in a subject in need thereof, the method comprising administering to the subject the pharmaceutical composition of claim 13.

19. The method according to claim 18, wherein the subject is in need of treatment of rheumatic arthritis or rheumatoid arthritis.

* * * * *